US012232734B2

(12) United States Patent
Rose et al.

(10) Patent No.: US 12,232,734 B2
(45) Date of Patent: Feb. 25, 2025

(54) INDEPENDENTLY POWERED ANVIL FOR CIRCULAR SURGICAL STAPLER

(71) Applicant: Cilag GmbH International, Zug (CH)

(72) Inventors: Logan R Rose, Loveland, OH (US);
Sean M Starrett, Columbus, OH (US);
Bradley A Arnold, Mason, OH (US);
Matthew D Cowperthwait, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/357,346

(22) Filed: Jul. 24, 2023

(65) Prior Publication Data

US 2025/0032119 A1     Jan. 30, 2025

(51) Int. Cl.
| | | |
|---|---|---|
| A61B 17/064 | (2006.01) | |
| A61B 17/115 | (2006.01) | |
| A61B 17/00 | (2006.01) | |
| A61B 90/00 | (2016.01) | |

(52) U.S. Cl.
CPC . A61B 17/1155 (2013.01); *A61B 2017/00221* (2013.01); *A61B 2090/064* (2016.02)

(58) Field of Classification Search
CPC .................................................. A61B 17/1155
See application file for complete search history.

(56) References Cited

U.S. PATENT DOCUMENTS

| | | |
|---|---|---|
| 5,205,459 A | 4/1993 | Brinkerhoff et al. |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,292,053 A | 3/1994 | Bilotti et al. |
| 5,333,773 A | 8/1994 | Main et al. |
| 5,350,104 A | 9/1994 | Main et al. |
| 5,533,661 A | 7/1996 | Main et al. |

(Continued)

FOREIGN PATENT DOCUMENTS

| | | |
|---|---|---|
| EP | 3108823 A2 | 12/2016 |
| WO | 2019/130087 A1 | 7/2019 |
| WO | 2022/189934 A1 | 9/2022 |

OTHER PUBLICATIONS

European Search Report, Partial, and Provisional Written Opinion dated Nov. 25, 2024 for Application No. EP 24190195.8, 17 pgs.

*Primary Examiner* — Eyamindae C Jallow
(74) *Attorney, Agent, or Firm* — Frost Brown Todd LLP

(57) ABSTRACT

A surgical stapler including a body assembly; a shaft assembly that extends distally from the body assembly; a stapling head assembly disposed at a distal end of the shaft assembly, wherein the stapling head assembly is operable to drive a plurality of staples into tissue, wherein the stapling head assembly comprises a closure shaft that is selectively movable longitudinally; and an anvil configured to form the staples, wherein the anvil is selectively coupleable with and actuatable by the closure shaft, wherein the anvil includes one or more sensors each configured to detect a parameter associated with at least one of closure or firing of the end effector; a processor configured to receive signals from the one or more sensors, wherein the signals are indicative of the parameter detected by the one or more sensors; a transmitter configured to transmit the signals; and a battery configured to power the processor.

20 Claims, 13 Drawing Sheets

(56) References Cited

U.S. PATENT DOCUMENTS

| | | |
|---|---|---|
| 8,910,847 B2 | 12/2014 | Nalagatla et al. |
| 9,597,081 B2 | 3/2017 | Swayze et al. |
| 9,713,469 B2 | 7/2017 | Leimbach et al. |
| 9,907,552 B2 | 3/2018 | Measamer et al. |
| 9,936,949 B2 | 4/2018 | Measamer et al. |
| 10,307,157 B2 | 6/2019 | Miller et al. |
| 10,709,452 B2 | 7/2020 | DiNardo et al. |
| 11,116,508 B2 * | 9/2021 | Adams ............. A61B 17/07207 |
| 11,490,891 B2 | 11/2022 | Rose et al. |
| 2015/0083772 A1 | 3/2015 | Miller et al. |
| 2016/0374672 A1 * | 12/2016 | Bear ........................ H02J 7/00 |
| | | 606/219 |
| 2017/0258471 A1 * | 9/2017 | DiNardo .............. A61B 17/072 |
| 2018/0310939 A1 * | 11/2018 | Stager ................ A61B 17/1155 |
| 2020/0281592 A1 * | 9/2020 | Adams ............... A61B 17/1155 |
| 2020/0281593 A1 * | 9/2020 | Adams .................. A61B 90/08 |
| 2020/0281594 A1 * | 9/2020 | Adams ................ A61B 17/1114 |
| 2020/0281595 A1 * | 9/2020 | Wise .................. A61B 17/1114 |
| 2020/0281596 A1 * | 9/2020 | Wise ................ A61B 17/07207 |
| 2022/0104806 A1 | 4/2022 | Shelton, IV et al. |

* cited by examiner

INDEPENDENTLY POWERED ANVIL FOR CIRCULAR SURGICAL STAPLER

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis, an end-to-side anastomosis, or a side-to-side anastomosis. The anastomosis may provide a substantially unobstructed flow path from one portion of the digestive tract to the other portion of the digestive tract, without also providing any kind of leaking at the site of the anastomosis.

One example of an instrument that may be used to provide an anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910, 847, entitled "Low Cost Anvil Assembly for a Circular Stapler," issued Dec. 16, 2014. The disclosure of each of the above-cited U.S. Patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015; U.S. Pat. No. 9,936, 949, entitled "Surgical Stapling Instrument with Drive Assembly Having Toggle Features," issued Apr. 10, 2018; U.S. Pat. No. 9,907,552, entitled "Control Features for Motorized Surgical Stapling Instrument," issued Mar. 6, 2018; U.S. Pat. No. 9,713,469, entitled "Surgical Stapler with Rotary Cam Drive," issued Jul. 25, 2017; and U.S. Pub. No. 2017/0258471, entitled "Methods and Systems for Performing Circular Stapling," published Sep. 14, 2017. The disclosure of each of the above-cited U.S. Patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
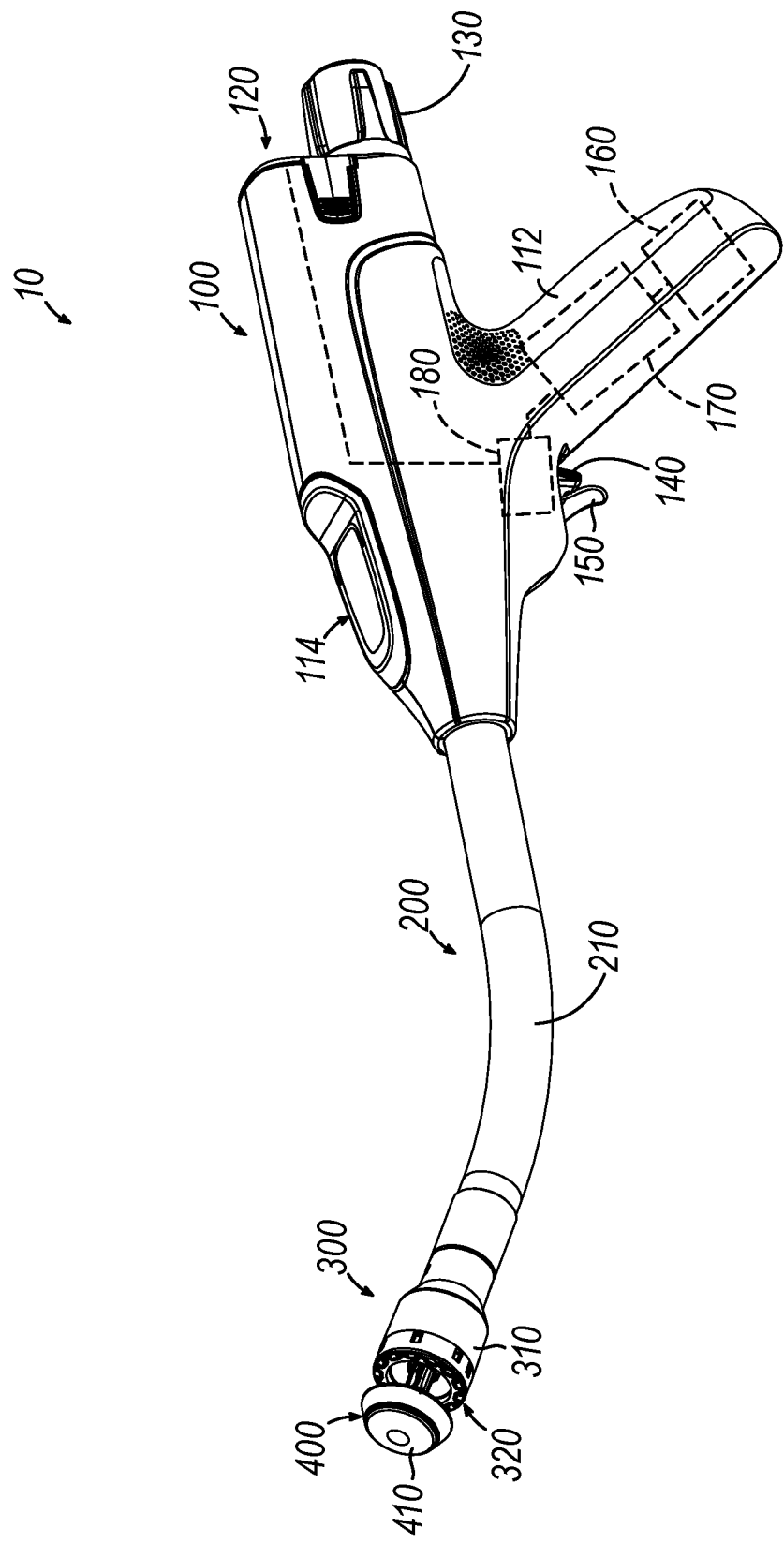
FIG. 1 depicts a perspective view of an illustrative circular surgical stapler.

The drawings are not intended to be limiting in any way, and it is contemplated that various embodiments of the technology may be carried out in a variety of other ways, including those not necessarily depicted in the drawings.

The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," "horizontal," or the like are used herein with reference to the drawings, it will be appreciated that such terms are used for illustrative description purposes only and are not intended to be limiting or absolute. In that regard, it will be understood that surgical instruments such as those disclosed herein may be used in a variety of orientations and positions not limited to those shown and described herein.

I. Overview of Illustrative Circular Surgical Stapling Instrument

Figure 2:
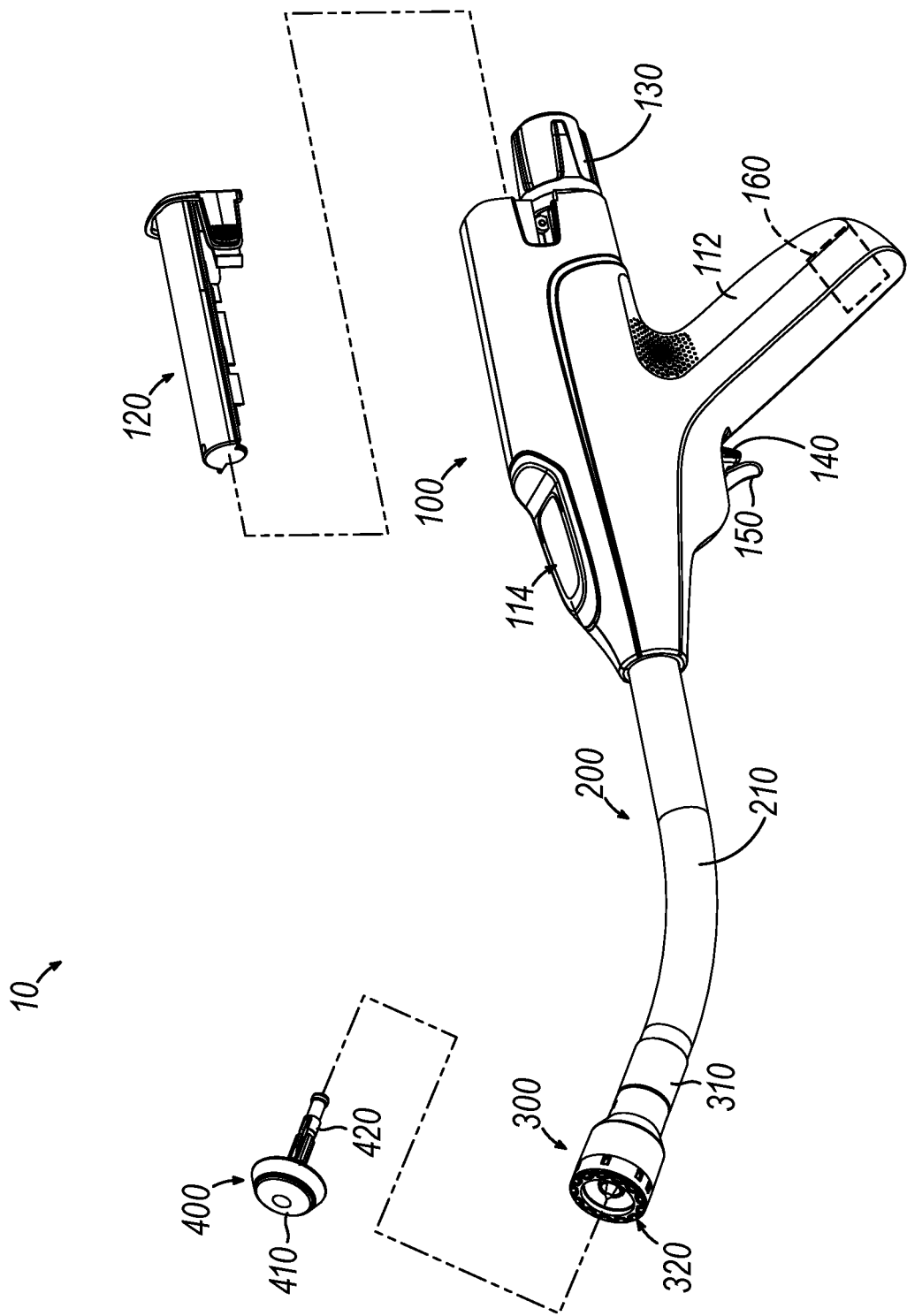
FIG. 2 depicts a perspective view of the circular stapler of FIG. 1, with a battery pack removed from a handle assembly and an anvil removed from a stapling head assembly.

FIGS. 1-2 depict an illustrative circular surgical stapling instrument (10) that may be used to provide an end-to-end, side-to-side, or end-to-side anastomosis between two sections of an anatomical lumen such as a portion of a patient's digestive tract. Instrument (10) of this example includes a body assembly (e.g. a handle assembly (100)), a shaft assembly (200) extending distally from handle assembly (100), a stapling head assembly (300) at a distal end of shaft assembly (200), and an anvil (400) configured to releasably couple and cooperate with stapling head assembly (300) to clamp, staple, and cut tissue. Instrument (10) further includes a removable battery pack (120) operable to provide electrical power to a motor (160) housed within handle assembly (100), as will be described in greater detail below, and a control module (170) housed within handle assembly (100) and configured to control motor (160) based on user input.

Shaft assembly (200) extends distally from handle assembly (100) and includes a preformed bend. In some versions, the preformed bend is configured to facilitate positioning of stapling head assembly (300) within a patient's colon. Various suitable bend angles or radii that may be used will be apparent to those skilled in the art in view of the teachings herein. In some other versions, shaft assembly (200) is straight, such that shaft assembly (200) lacks a preformed bend. Various illustrative components that may be incorporated into shaft assembly (200) will be described in greater detail below.

Stapling head assembly (300) is located at the distal end of shaft assembly (200). As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A knob (130) at the proximal end of handle assembly (100) is rotatable relative to casing (110) to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the tissue.

A. Illustrative Anvil

Figure 3:
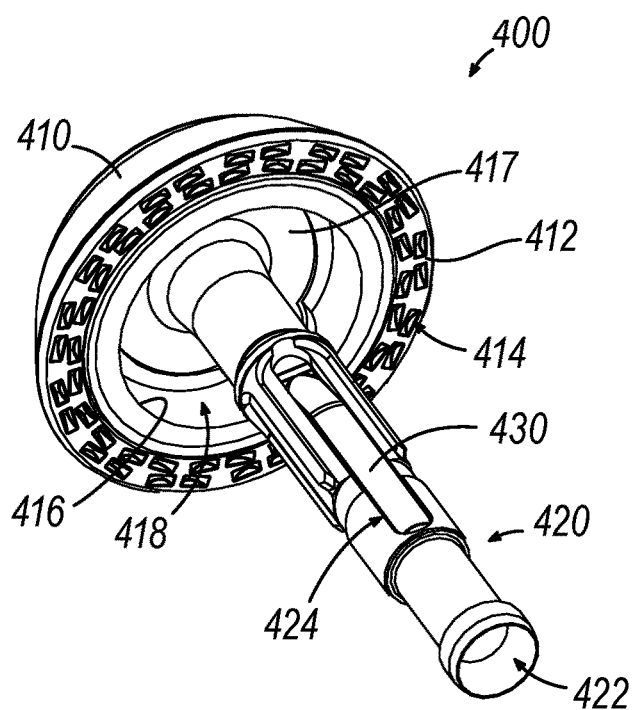
FIG. 3 depicts a perspective view of the anvil of the circular stapler of FIG. 1.

As best seen in FIG. 3, anvil (400) of the present example comprises a head (410) and a shank (420). Head (410) includes a proximal surface (412) that defines a plurality of staple forming pockets (414). Staple forming pockets (414) are arranged in two concentric annular arrays in the present example. In some other versions, staple forming pockets (414) are arranged in three or more concentric annular arrays. Staple forming pockets (414) are configured to deform staples as the staples are driven into staple forming pockets (414). For instance, each staple forming pocket (414) may deform a generally "U" shaped staple into a "B" shape as is known in the art. Proximal surface (412) terminates at an inner edge (416), which defines an outer boundary of an annular recess (418) surrounding shank (420).

Shank (420) defines a bore (422) and includes a pair of pivoting latch members (430). Latch members (430) are positioned within bore (422) such that the distal ends are positioned at the proximal ends of lateral openings (424), which are formed through the sidewall of shank (420). Lateral openings (424) thus provide clearance for the distal ends and latch shelves (436) to deflect radially outwardly from the longitudinal axis defined by shank (420). However, latch members (430) are configured to resiliently bias the distal ends and latch shelves (436) to pivot radially inwardly toward the longitudinal axis defined by shank (420). Latch members (430) thus act as retaining clips. This allows anvil (400) to be removably secured to an actuatable closure member (also referred to a closure shaft) in the form of a trocar (330) of stapling head assembly (300), as will be described in greater detail below. It should be understood, however, that latch members (436) are merely optional. Anvil (400) may be removably secured to trocar (330) using any other suitable components, features, or techniques.

B. Illustrative Stapling Head Assembly

Figure 4:
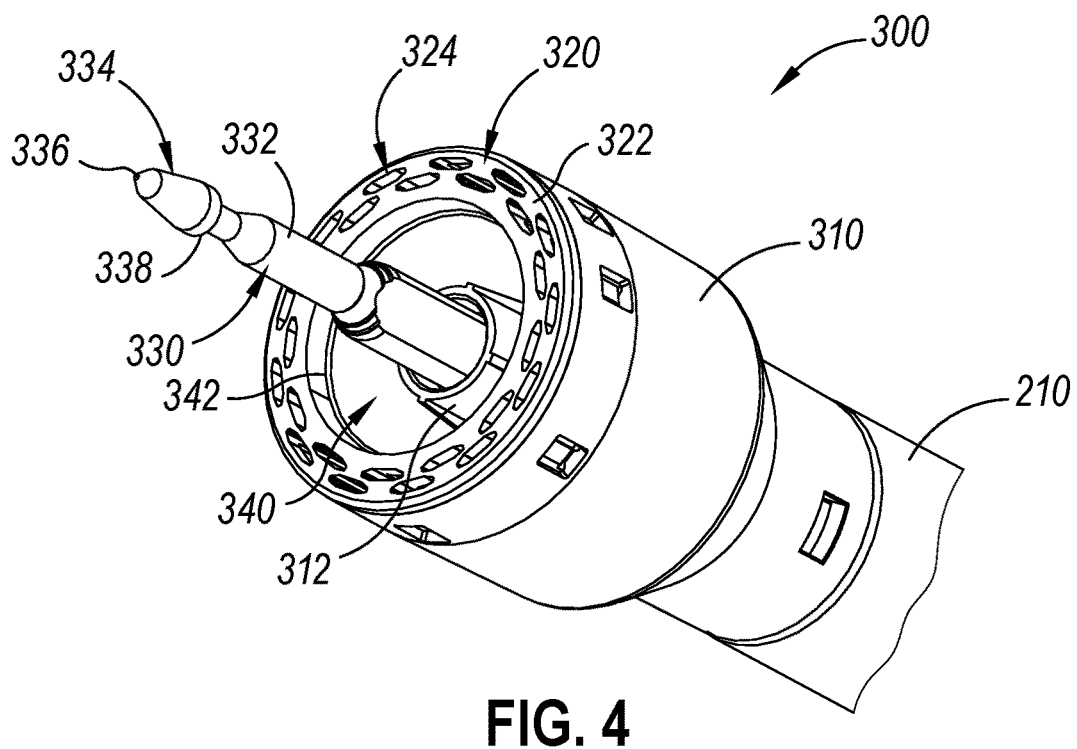
FIG. 4 depicts a perspective view of the stapling head assembly of the circular stapler of FIG. 1.
Figure 5:
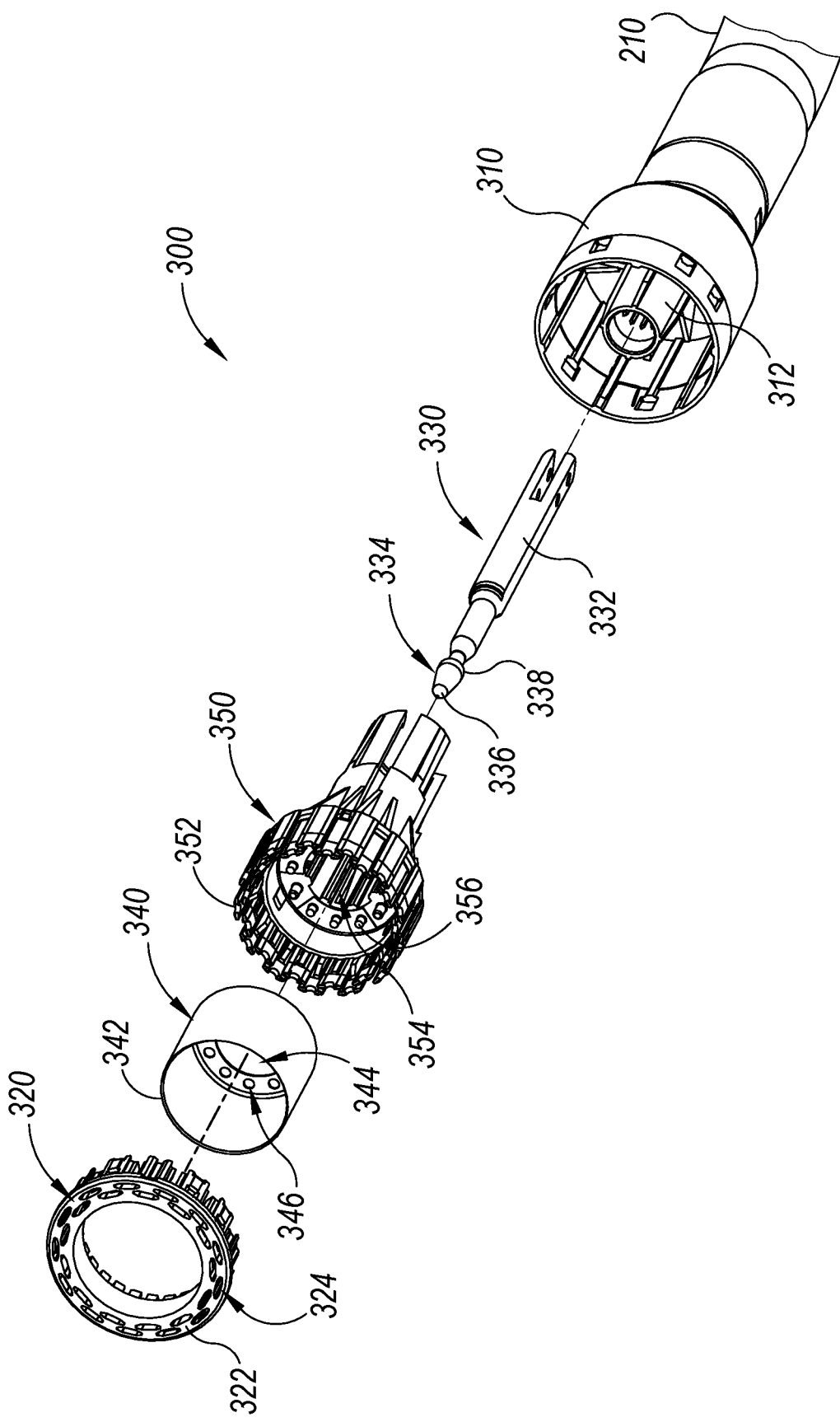
FIG. 5 depicts an exploded perspective view of the stapling head assembly of FIG. 4.

As best seen in FIGS. 4 and 5, stapling head assembly (300) of the present example is coupled to a distal end of shaft assembly (200) and comprises a body member (310) and a staple driver member (350) slidably housed therein. Body member (310) includes a distally extending cylindraceous inner core member (312). Body member (310) is fixedly secured to an outer sheath (210) of shaft assembly (200), and body member (310) and outer sheath (210) thus serve together as a mechanical ground for stapling head assembly (300). In some versions, stapling head assembly (300) may be configured to releasably couple with the distal end of shaft assembly (200), for example as disclosed in U.S. Pat. No. 9,597,081, entitled "Motor Driven Rotary Input Circular Stapler with Modular End Effector," issued Mar. 21, 2017, the disclosure of which is incorporated by reference herein.

Trocar (330) is positioned coaxially within inner core member (312) of body member (310). As will be described in greater detail below, trocar (330) is operable to translate distally and proximally relative to body member (310) in response to rotation of knob (130) relative to casing (110) of handle assembly (100). Trocar (330) comprises a shaft (332) and a head (334). Head (334) includes a pointed tip (336) and an inwardly extending proximal surface (338). Shaft (332) thus provides a reduced outer diameter just proximal to head (334), with surface (338) providing a transition between that reduced outer diameter of shaft (332) and the outer diameter of head (334). While tip (336) is pointed in the present example, tip (336) is not sharp. Tip (336) will thus not easily cause trauma to tissue due to inadvertent contact with tissue. Head (334) and the distal portion of shaft (332) are configured for insertion in bore (422) of anvil (400). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit provided by latch members (430).

Staple driver member (350) is operable to actuate longitudinally within body member (310) in response to activation of motor (160) as will be described in greater detail below. Staple driver member (350) of the present example includes two distally presented concentric annular arrays of staple drivers (352). Staple drivers (352) are arranged to correspond with the arrangement of staple forming pockets (414) of anvil (400). Thus, each staple driver (352) is configured to drive a corresponding staple into a corresponding staple forming pocket (414) when stapling head assembly (300) is actuated. It should be understood that the arrangements of staple drivers (352) and staple forming pockets (414) shown herein may be modified in any suitable manner, provided that staple drivers (352) and staple forming pockets (414) are configured to align with one another to provide proper formation of staples. Staple driver member (350) also defines a bore (354) that is configured to coaxially receive core member (312) of body member (310). An annular array of studs (356) project distally from a distally presented surface surrounding bore (354).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of body member (310). An annular array of openings (346) formed in knife member (340) is configured to complement the annular array of studs (356) of staple driver member (350), such that knife member (340) is fixedly secured to staple driver member (350) via studs (356) and openings (346). By way of example only, studs (356) may be heat staked to knife member (340) using techniques known in the art. Other suitable structural relationships between knife member (340) and stapler driver member (350) will be apparent to those skilled in the art in view of the teachings herein.

A deck member (320) is fixedly secured to a distal end of body member (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should be understood that the arrangement of staple openings (324) may be modified to correspond with the arrangement of drivers (352) and staple forming pockets (414) described above. It should also be understood that various structures and techniques may be used to contain staples within stapling head assembly (300) before stapling head assembly (300) is actuated. Such structures and techniques that are used to contain staples within stapling head assembly (300) may prevent the staples from inadvertently falling out through staple openings (324) before stapling head assembly (300) is actuated. Various suitable forms that such structures and techniques may take will be apparent to those skilled in the art in view of the teachings herein.

Referring to FIG. 5, deck member (320) defines an inner diameter that is just slightly larger than the outer diameter defined by knife member (340). Deck member (320) is thus configured to allow knife member (340) to translate distally to a point where cutting edge (342) is distal to deck surface (322).

In some versions of instrument (10) it may be desirable to provide instrument (10) with features that are configured to indicate proper and/or improper attachment of anvil (400) to trocar (330) of stapling head assembly (300). For instance, if anvil (400) is not properly attached to trocar (330), an operator may receive audible and/or tactile feedback indicating improper attachment. Additionally, if anvil (400) is properly attached to trocar (330), an operator may receive audible, tactile, and/or visible feedback indicating proper attachment. In addition, or in the alternative, features may be configured to prevent firing of stapling head assembly (300) unless anvil (400) is properly attached to trocar (330). For instance, if anvil (400) is not properly attached to trocar (330), stapling head assembly (300) may be prevented from firing. If anvil (400) is properly attached to trocar (330), firing of stapling head assembly (300) may be enabled. Such features may include various types of visual indicia, sensors, switches, and the like. By way of example only, such features may include those of the type disclosed in U.S. Pat. No. 10,307,157, entitled "Surgical Stapler with Anvil Seating Detection," issued Jun. 4, 2019, and U.S. Pub. No. 2017/0258471, entitled "Methods and Systems for Performing Circular Stapling," published Sep. 14, 2017, the disclosures of which are incorporated by reference herein.

C. Illustrative Shaft Assembly

Figure 6:
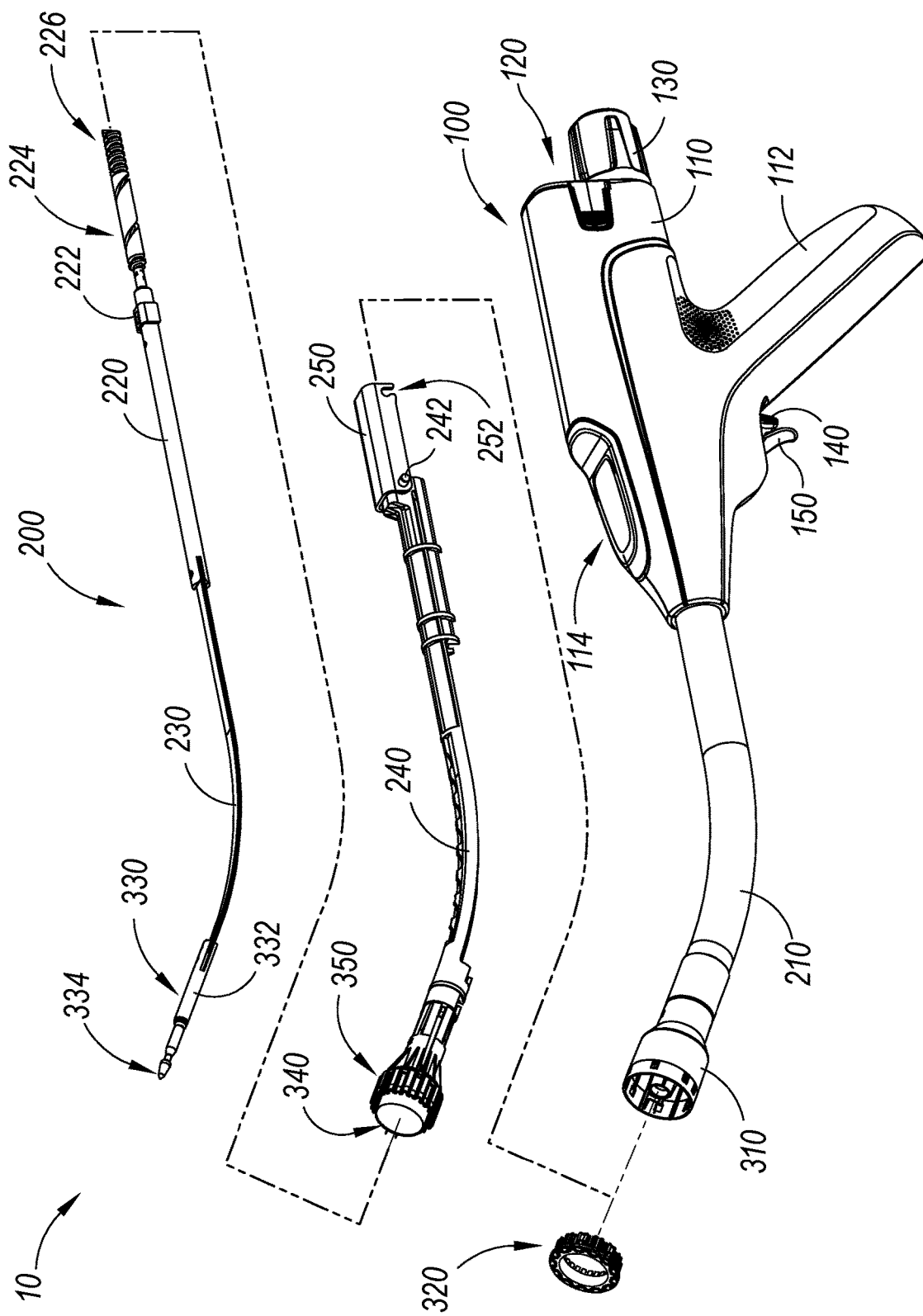
FIG. 6 depicts an exploded perspective view of the circular stapler of FIG. 1, with portions of the shaft assembly shown separated from each other.

FIG. 6 shows various components of shaft assembly (200), which couples components of stapling head assembly (300) with components of handle assembly (100). In particular, and as noted above, shaft assembly (200) includes an outer sheath (210) that extends between handle assembly (100) and body member (310). In the present example, outer sheath (210) is rigid and includes a preformed curved section as noted above.

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220). It should therefore be understood that trocar (330)

will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226).

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350).

D. Illustrative Handle Assembly and User Input Features

As shown in FIG. 1, handle assembly (100) includes a casing (110) having a lower portion that defines an obliquely oriented pistol grip (112) and an upper portion that supports a user interface feature (114) and receives a battery pack (120), as described in greater detail below. Handle assembly (100) further includes several features that are operable to actuate anvil (400) and stapling head assembly (300). In particular, handle assembly (100) includes a rotatable knob (130), a safety trigger (140) a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, then translate proximally at a relatively fast rate, in response to rotation of knob (130).

It should be understood that when anvil (400) is coupled with trocar (330), rotation of knob (130) will provide corresponding translation of anvil (400) relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (400) away from stapling head assembly (300). Knob (130) may thus be used to adjust a gap distance (d) between opposing surfaces (412, 322) of anvil (400) and stapling head assembly (300) until a suitable gap distance (d) has been achieved, for example as shown in FIG. 7C described below.

Firing trigger (150) is operable to activate motor (160) to thereby actuate stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). For instance, safety trigger (140) may be blocked from rotating from an engaged position to a disengaged position until the position of anvil (400) relative to stapling head assembly (300) is within a predefined range. Accordingly, until the anvil position is within the predefined range, actuation of firing trigger (150) is blocked by safety trigger (140), thereby inhibiting firing of stapling head assembly (300).

Firing trigger (150) of the present example includes an integral actuation paddle (not shown), which may be similar to the paddle disclosed in U.S. Pub. No. 2017/0258471, incorporated by reference above. The paddle is configured to actuate a switch of motor activation module (180) (FIG. 1) when firing trigger (150) is pivoted to a fired position. Motor activation module (180) is in communication with battery pack (120) and motor (160), such that motor activation module (180) is configured to provide activation of motor (160) with electrical power from battery pack (120) in response to the paddle actuating the switch of motor activation module (180). Thus, motor (160) will be activated when firing trigger (150) is pivoted. This activation of motor (160) will actuate stapling head assembly (300) via drive bracket (250), as described in greater detail below. Though not shown, and by way of example only, motor (160) may be operatively coupled with drive bracket (250) via a gearbox coupled with an output shaft of motor (160), a rotary cam member coupled with an output shaft of the gearbox, and a cam follower coupled with the rotary cam member, for example as disclosed in U.S. Pub. No. 2017/0258471, incorporated by reference above.

As best shown in FIGS. 1-2, handle assembly (100) is further configured to releasably receive a battery pack (120) operable to provide electrical power to motor (160), as noted above. It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is coupled with handle assembly (100). It should also be understood that, in some versions, battery pack (120) may be unitarily integrated within handle assembly (100) such that battery back (120) cannot be removed from handle assembly (100).

E. Illustrative Anastomosis Procedure with Circular Stapling Instrument

FIGS. 7A-7E show instrument (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures. In some versions, one or more diseased portions of a patient's colon are removed, with the tubular anatomical structures (20, 40) of FIGS. 7A-7E representing the remaining severed portions of the colon.

Figure 7A:
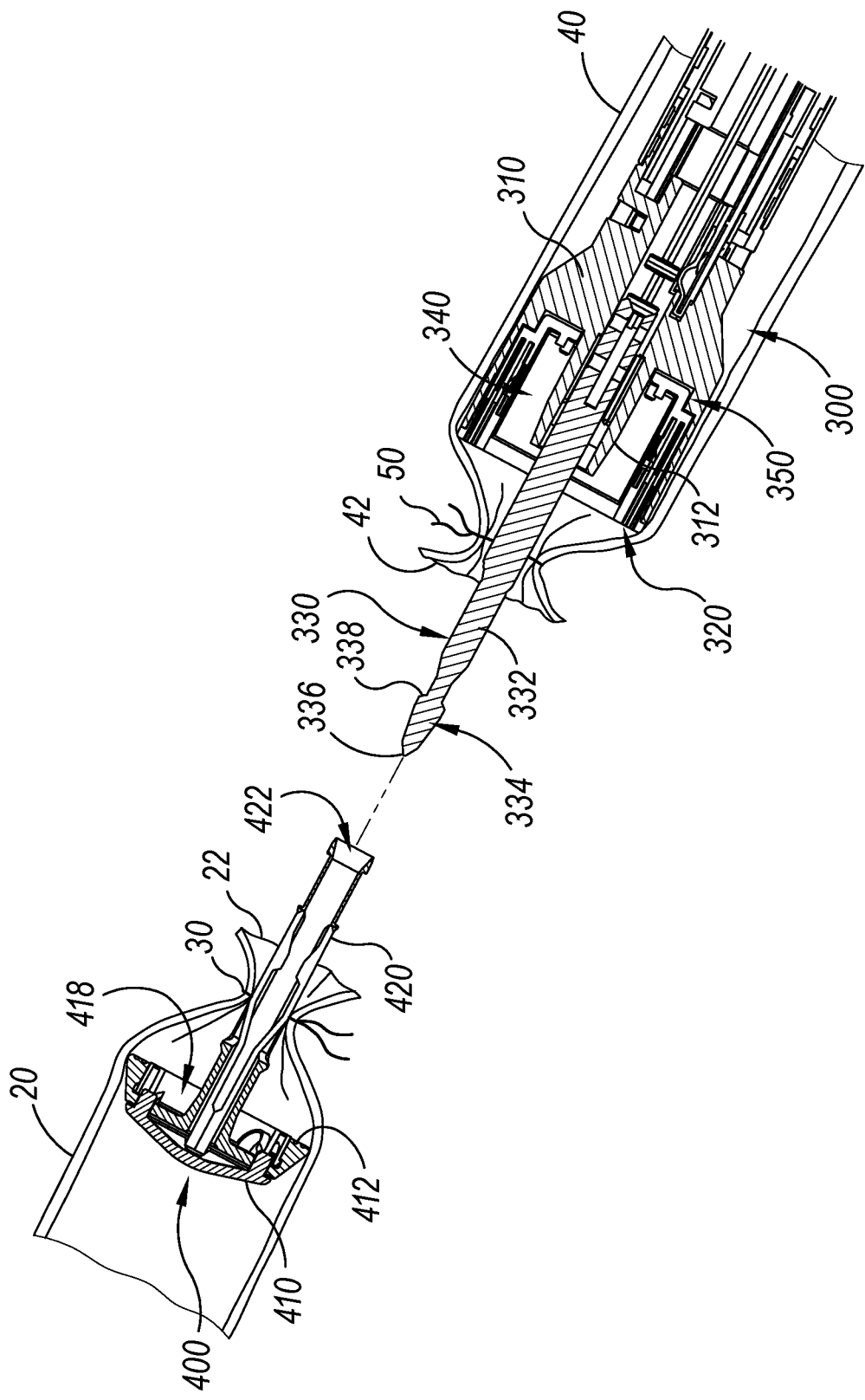
FIG. 7A depicts a cross-sectional side view of the anvil of FIG. 3 positioned within a first section of a digestive tract and the stapling head assembly of FIG. 4 positioned in a second section of the digestive tract, with the anvil separated from the stapling head assembly.

As shown in FIG. 7A, anvil (400) is positioned in one tubular anatomical structure (20) and stapling head assembly (300) is positioned in another tubular anatomical structure (40). In versions where tubular anatomical structures (20, 40) comprise sections of a patient's colon, stapling head assembly (300) may be inserted via the patient's rectum. It should also be understood that the procedure depicted in FIGS. 7A-7E is an open surgical procedure, though the procedure may instead be performed laparoscopically. Various suitable ways in which instrument (10) may be used to form an anastomosis (70) in a laparoscopic procedure will be apparent to those skilled in the art in view of the teachings herein.

As shown in FIG. 7A, anvil (400) is positioned in tubular anatomical structure (20) such that shank (420) protrudes from the open severed end (22) of tubular anatomical structure (20). In the present example, purse-string suture (30) is provided about a mid-region of shank (420) to generally secure the position of anvil (400) in tubular anatomical structure (20). In some other variations, purse-string suture (30) is tightened around the proximal end of shank (420). In some such variations, the proximal end of shank (420) may include a notch or other feature to securely capture purse-string suture (30). Continuing with the present example, stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40). Stapling head assembly (300) is then urged distally to ensure that stapling head assembly (300) is fully seated at the distal end of tubular anatomical structure (40).

Figure 7B:
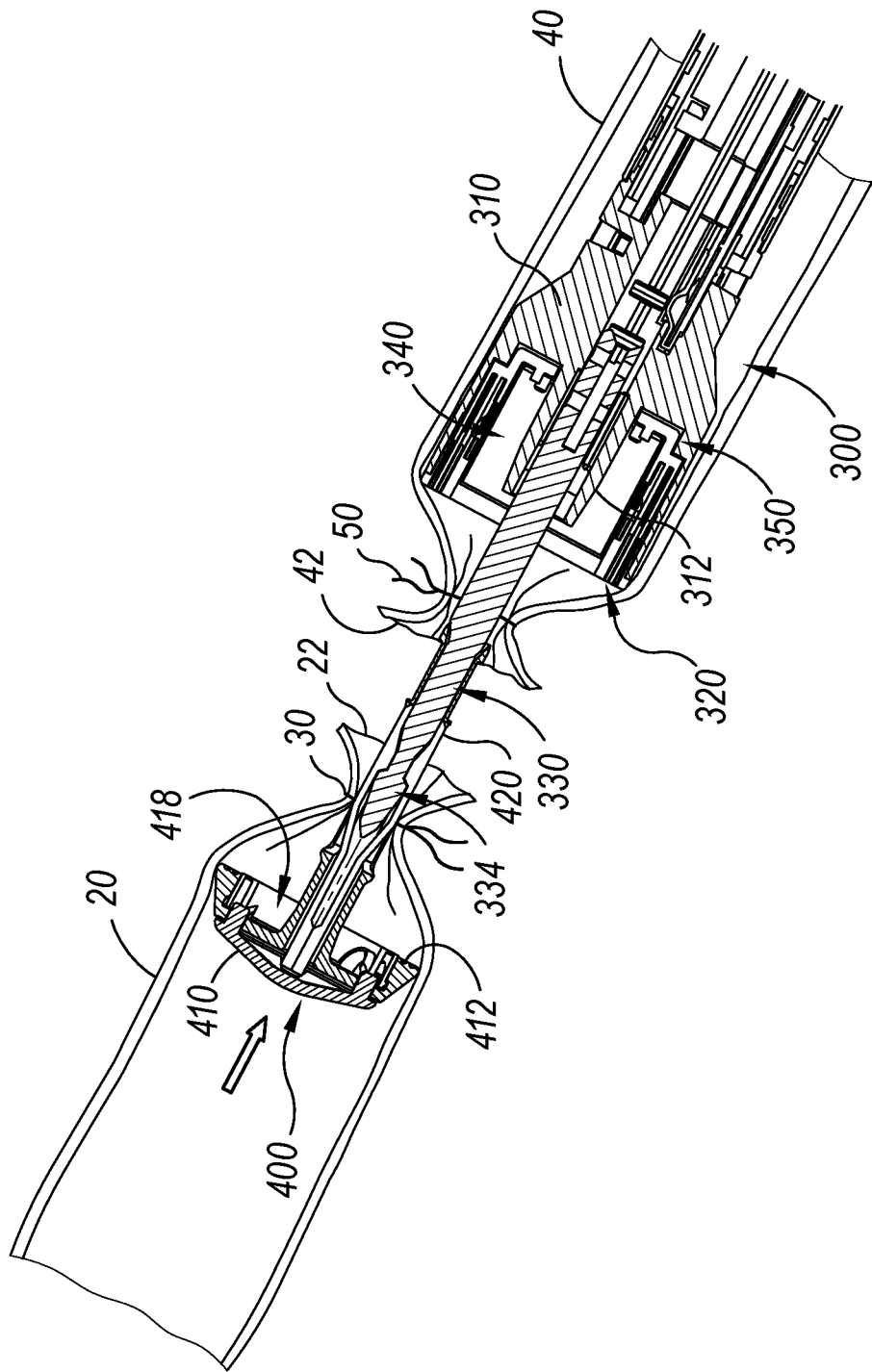
FIG. 7B depicts a cross-sectional side view of the anvil of FIG. 3 positioned within the first section of the digestive tract and the stapling head assembly of FIG. 4 positioned in the second section of the digestive tract, with the anvil secured to the stapling head assembly.
Figure 7C:
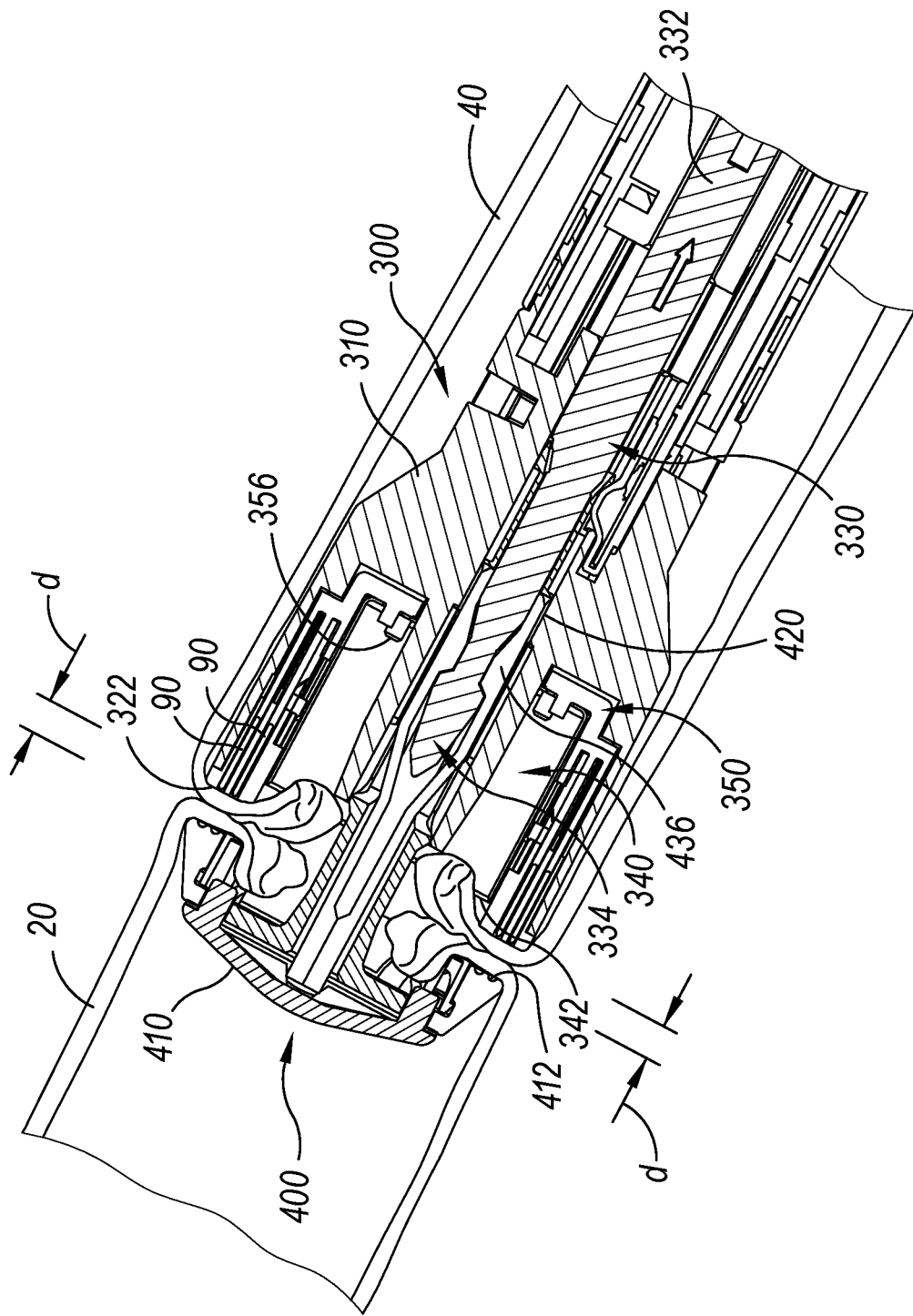
FIG. 7C depicts a cross-sectional side view of the anvil of FIG. 3 positioned within the first section of the digestive tract and the stapling head assembly of FIG. 4 positioned in the second section of the digestive tract, with the anvil retracted toward the stapling head assembly to thereby clamp tissue between the anvil and the stapling head assembly.

Next, anvil (400) is secured to trocar (330) by inserting trocar (330) into bore (422) as shown in FIG. 7B. Latch members (430) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally. As shown in FIG. 7C, this proximal retraction of trocar (330) and anvil (400) compresses the tissue of tubular anatomical structures (20, 40) between surfaces (412, 322) of anvil (400) and stapling head assembly (300). As this occurs, the operator may observe the tactile resistance or feedback via knob (130) while turning knob (130), with such tactile resistance or feedback indicating that the tissue is being compressed. As the tissue is being compressed, the operator may visually observe the position of an indicator needle (522) within a user interface feature (114) of handle assembly (100) to determine whether the gap distance (d) between opposing surfaces (412, 322) of anvil (400) and stapling head assembly (300) is appropriate; and make any necessary adjustments via knob (130).

Figure 7D:
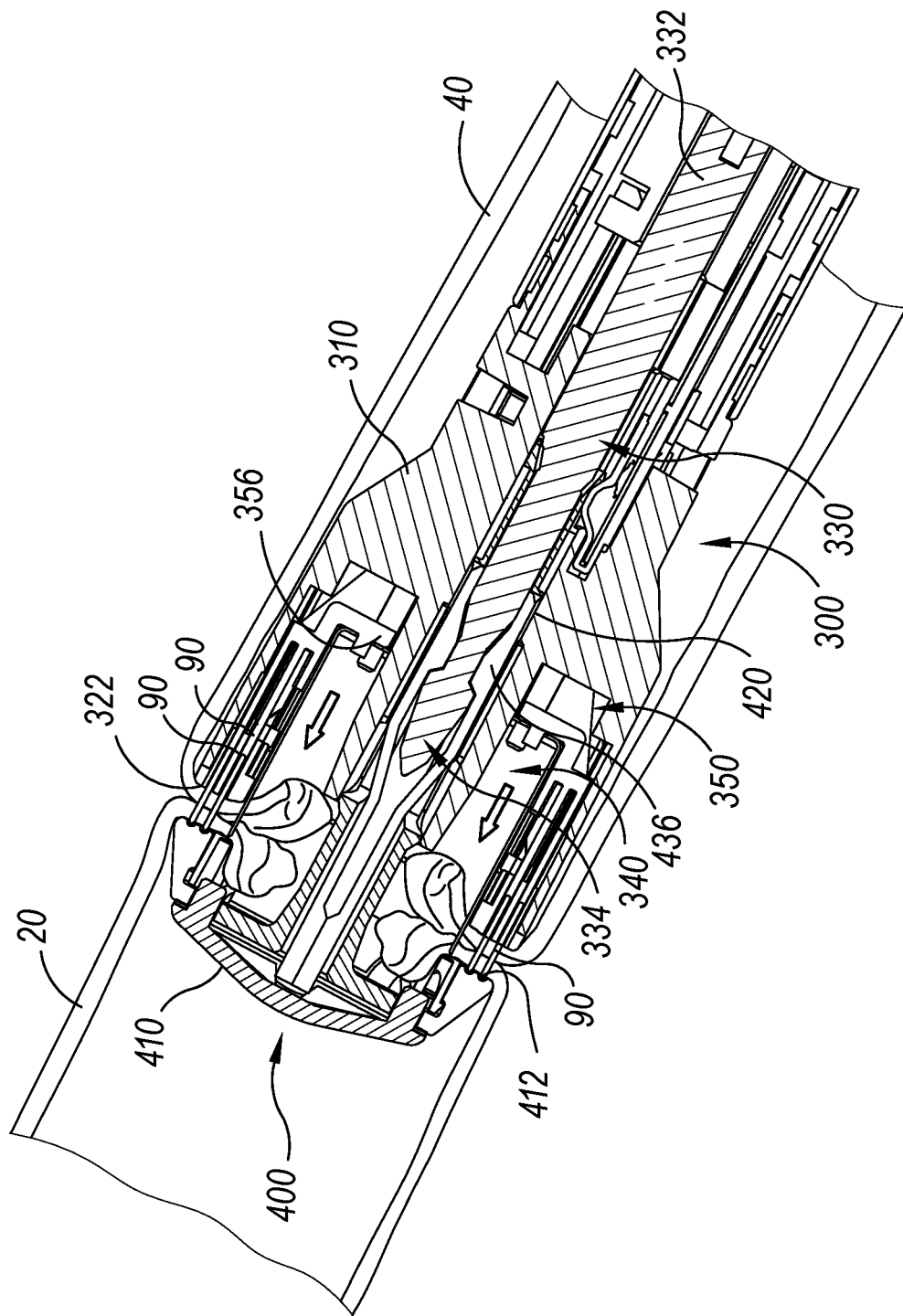
FIG. 7D depicts a cross-sectional side view of the anvil of FIG. 3 positioned within the first section of the digestive tract and the stapling head assembly of FIG. 4 positioned in the second section of the digestive tract, with the stapling head assembly actuated to sever and staple the clamped tissue.

Once the operator has appropriately set the gap distance (d) via knob (130), the operator pivots safety trigger (140) toward pistol grip (112) to enable actuation of firing trigger (150). The operator then pivots firing trigger (150) toward pistol grip (112), thus causing paddle (not shown) to actuate the switch of motor activation module (180) and thereby activate motor (160) to rotate. This rotation of motor (160) causes actuation (or "firing") of stapling head assembly (300) by actuating drive bracket (250) distally to thereby drive knife member (340) and staple driver member (350) distally, as shown in FIG. 7D. As knife member (340) translates distally, cutting edge (342) of knife member (340) cuts excess tissue that is positioned within annular recess (418) of anvil (400) and the interior of knife member (340).

As shown in FIG. 3, anvil (400) of the present example includes a breakable washer (417) positioned within annular recess (418). This washer (417) is broken by knife member (340) when the knife member (340) completes a full distal range of motion from the position shown in FIG. 7C to the position shown in FIG. 7D. Features of stapler (10) may be configured to provide an increasing mechanical advantage as knife member (340) reaches the end of its distal movement, thereby providing greater force by which to break the washer (417). Of course, the breakable washer (417) may be omitted entirely in some versions. In versions where washer (417) is included, it should be understood that washer (417) may also serve as a cutting board for knife member (340) to assist in cutting of tissue.

As staple driver member (350) translates distally from the position shown in FIG. 7C to the position shown in FIG. 7D, staple driver member (350) drives staples (90) through the tissue of tubular anatomical structures (20, 40) and into staple forming pockets (414) of anvil (400). Staple forming pockets (414) deform the driven staples (90) into a "B" shape or a three-dimensional shape, for example, such that the formed staples (90) secure the ends of tissue together, thereby coupling tubular anatomical structure (20) with tubular anatomical structure (40).

Figure 7E:
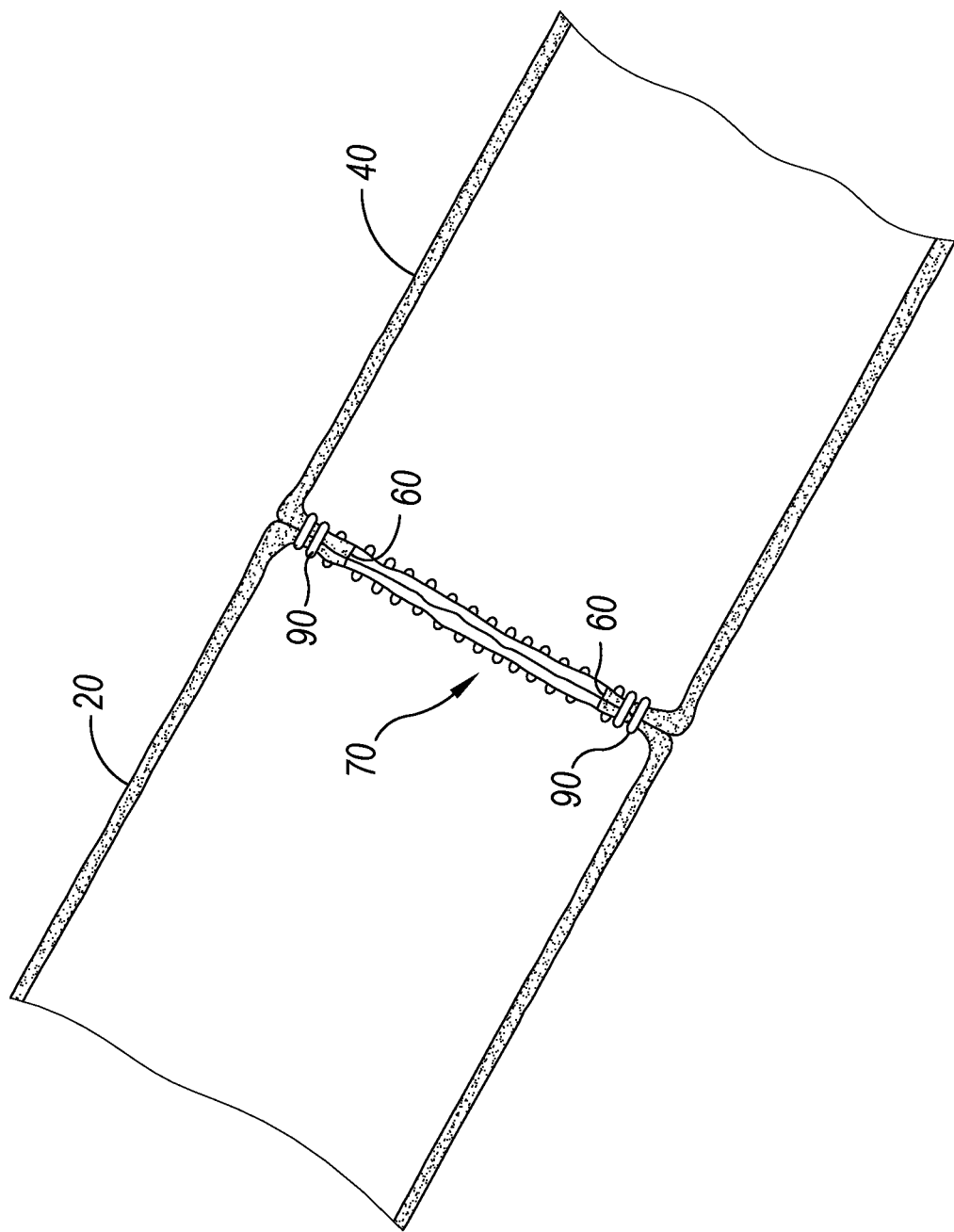
FIG. 7E depicts a cross-sectional side view of the first and second sections of the digestive tract of FIG. 7A joined together at an end-to-end anastomosis.

After the operator has actuated stapling head assembly (300) as shown in FIG. 7D, the operator rotates knob (130) to drive anvil (400) distally away from stapling head assembly (300), increasing the gap distance (d) to facilitate release of the tissue between surfaces (412, 322). The operator then removes instrument (10) from the patient, with anvil (400) still secured to trocar (330). Referring back to the example where the tubular anatomical structures (20, 40) comprise sections of a patient's colon, instrument (10) may be removed via the patient's rectum. With instrument (10) removed, the tubular anatomical structures (20, 40) are left secured together by two annular arrays of staples (90) at an anastomosis (70) as shown in FIG. 7E. The inner diameter of the anastomosis (70) is defined by the severed edge (60) left by knife member (340).

II. Example Wireless Powered Anvil and Method of Use

In certain situations, it may be beneficial to transmit load and position data from the anvil to a controller that may be housed within remaining portions of the surgical stapler or outside of the surgical stapler, such as the control module/center taught in U.S. Pat. No. 11,490,891, entitled "Load Sensor for Circular Surgical Stapler," issued Nov. 8, 2022, which is hereby incorporated by reference herein, in its entirety. Furthermore, it may also be beneficial to remotely transmit load and position data from the anvil to a control center or a receiver.

As mentioned above, some features provide a way to confirm that the anvil is connected with the trocar, and other features provide a way to gauge the degree of staple formation based on the distance between the underside anvil surface having the stapling forming pockets and the deck surface having the staple openings. In some instances, it would be separately or additionally desirable to have the ability to confirm, prior to firing or driving staples, that the circumferential load being applied to the tissue is uniform or substantially uniform. In at least some versions, "substantially uniform" means that the load is within an acceptable level of variability where the quality of stapling head assembly (300) actuation avoids defects such as malformed staples; or where washer (417) is not completely broken by for knife member (340). Substantial uniformity in this respect will be apparent to those skilled in the art in view of the teachings herein.

Figure 8:
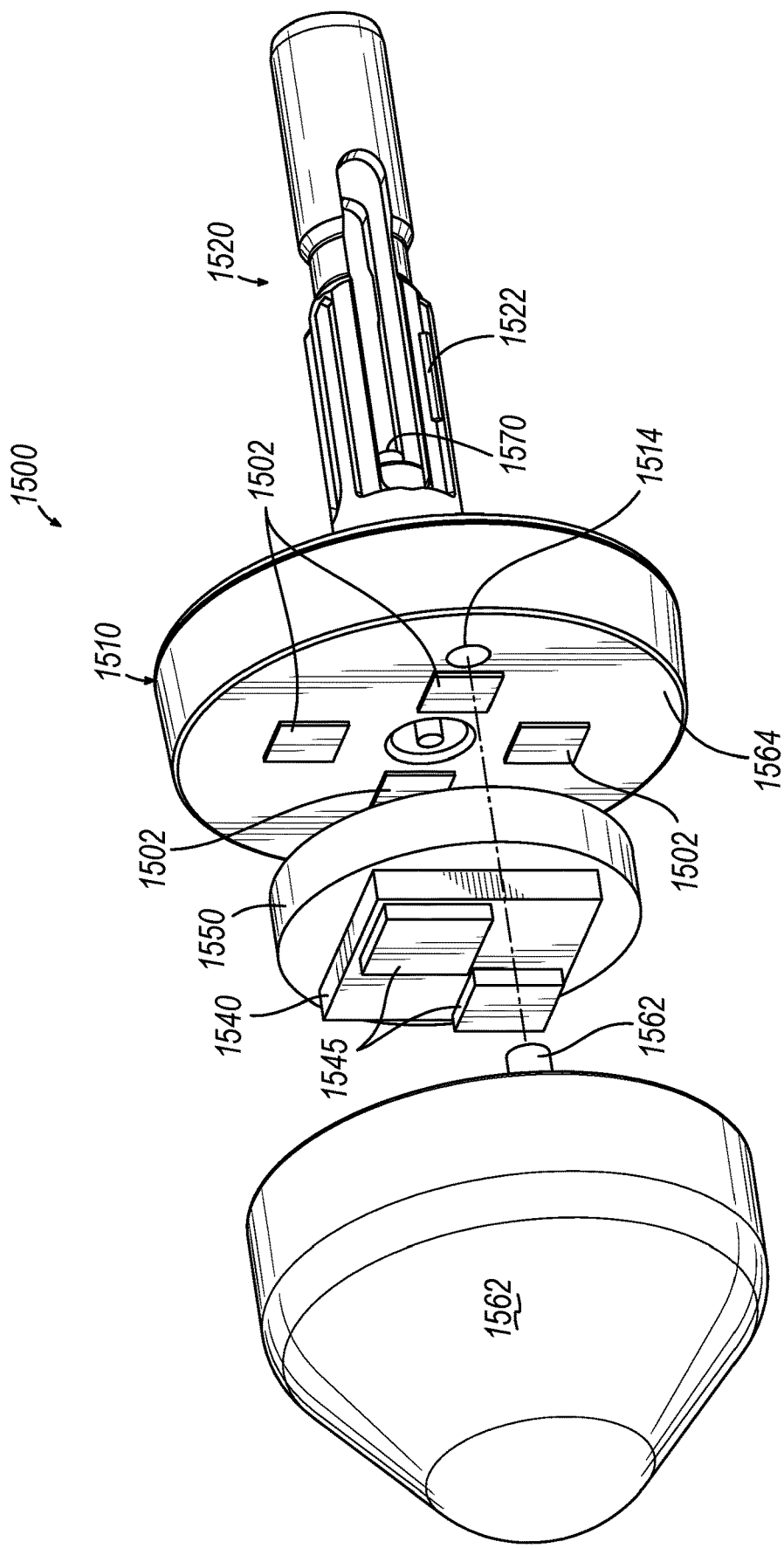
FIG. 8 depicts an exploded perspective view of an alternative anvil having a shroud that encloses certain electronic components of the anvil.

In some such situations, it may be desirable to utilize an anvil that is capable in the manner described above, and that is furthermore powered independently from the remainder of the circular stapler and is capable of wirelessly transmitting data to the controller, such that the anvil may be used with a variety of different circular staplers. FIGS. 8-9B show an illustrative alternative anvil that is configured and operable in such a manner, as described in greater detail below.

A. Wireless Powered Anvil

FIG. 8 illustrates an example of an anvil (1500) that is configured for use with instrument (10) and is substantially similar to anvil (400) and the anvils described in U.S. Pat. No. 11,490,891, which has been incorporated by reference above, except as otherwise described below. In some versions, anvil (1500) may be used with stapling head assembly (300) in place of anvil (400).

Anvil (1500) comprises a head (1510) and a shank (1520). Shank (1520) may be selectively coupled to trocar (330) and may include one or more shank sensors (1522). Shank sensors (1522) may be a strain gauge capable of measuring or determining strain within shank (1520) when anvil (1500) compresses tissue (12) against deck member (320). Shank sensors (1522) may be equally spaced circumferentially around shank (1520) such that they are capable of determining disproportionate amounts of strain throughout a cross-section of shank (1520). Shank sensors (1522) may include a wire or electric conduit that are routed distally to a proximal portion of head (1510) through a central opening in both shank (1520) and head (1510). Shank (1520) may include three or more shank sensors (1522). Shank sensor (1522) may comprise one or more load cells.

Head (1510) may include a distal surface which may include one more head sensors (1502) that are arranged circumferentially and are substantially similar to strain gauges (1402) of U.S. Pat. No. 11,490,891, incorporated by reference above. Head (1510) may include three or more head sensors (1502). Head sensor (1502) may comprise one or more load cells.

Anvil (1500) may further comprise a processor (1540), a transmitter (1545), a battery (1550), and a power switch (1570). Processor (1540) may be in electrical communication with each of the shank sensors (1522), head sensors (1502), transmitter (1546), battery (1550) and power switch (1570). Processor (1540) may be capable of performing the functions of control module (170) of U.S. Pat. No. 11,490,891. Processor (1540) may be capable of converting signals from shank sensors (1522), head sensors (1502), and battery (1550) into data signals and then communicating those data signals to transmitter (1545).

Head sensors (1502) and shank sensors (1522) may be substantially similar to strain gauges (1402) of U.S. Pat. No. 11,490,891 in that they may define loading zones. Each loading zone corresponds to the area or region surrounding and including a respective sensor (1502, 1522). Each sensor (1502, 1522) may be associated with a respective loading zone and may be operable to detect a parameter associated with the respective loading zone. As an example only, the parameter detected may be a strain associated with the respective loading zone. Head sensors (1502) and shank sensors (1522) may be capable of measuring a strain indicative of a force applied to the tissue during tissue compression and/or firing at either head (1510) or shank (1520), wherein such force is thus also experienced by the closure system components and firing system components of stapler (10). A predetermined threshold may be defined that represents an acceptable deviation from a median strain measured across all sensors (1502, 1522). Where any one of sensors (1502, 1522) measures a strain outside this predetermined threshold of strain deviation from the median, processor (1540) and/or control module (170) would output a result indicating that uniform loading has not been achieved, or in other words that there is an uneven or non-uniform load applied to the tissue between anvil (1500) and deck member (320).

Transmitter (1545) may be capable of receiving data signals from processor (1540) through an electrical conduit and wirelessly transmitting those data signals to an outside control module over a short-range wireless network. By way of example only, transmitter (1545) may be Bluetooth® or Wi-Fi capable and may be operable at a 2.45 or 5 GHz frequency. Transmitter (1545) may be positioned distal to battery (1550) and processor (1540) or in such a way that battery (1550) and processor (1540) do not interfere with the wireless transmission.

Battery (1550) may be in electrical communication with and capable of powering head sensors (1502), shank sensors (1522), processor (1540), transmitter (1545), and power switch (1570). Battery (1550) may be sized smaller than an outer diameter of head (1510) such that battery (1550) does not overhang from an outer edge of head (1510). Battery (1550) may include enough energy storage to power anvil (1500) throughout a procedure or operation. Battery (1550) may be positioned between head sensors (1502) and processor (1540) and may be mounted to head (1510) so as to not interfere with a reading of head sensors (1502). To accomplish this, battery (1550) may be spaced distally from head sensors (1502) while still being mounted to head (1510). Optionally, battery (1550) may be selectively removable and replaceable for continued use of anvil (1500).

Power switch (1570) may be positioned within or proximate to shank (1520) and directed proximally such that it is configured to transition between electrically open and closed configurations based on whether it is in contact with trocar (330) (shown schematically in FIGS. 9A-9B), or another feature of stapling head assembly (300). In other words, power switch (1570) may be configured to transition between an open state when anvil (1500) is coupled to trocar (330), and a closed state when anvil (1500) is decoupled from trocar (330). Power switch (1570) may be a normally-open or a normally-closed switch and may be a maintained or a momentary switch. An electrical contact of power switch (1570) may be positioned between battery (1550) and remaining electrical components of anvil (1500). In this manner, power switch (1570) may be transitioned into the closed configuration to power any of the remaining components and anvil (1500) may enter a high-power configuration. Alternatively, processor (1540) may be continuously in electrical communication with battery (1550), and processor (1540) may be configured to detect attachment of anvil (1510) to trocar (330) and thus enter the high-power configuration upon detecting such attachment.

When anvil (1500) is decoupled from stapling head assembly (300) such that power switch (1570) is not contacting trocar (330), anvil (1500) may remain in a low-power configuration in order to conserve energy and battery (1550) life. High-power configuration powers and makes operable the electrical components of anvil (1500). Power switch (1570) of a maintained type may be configured to maintain anvil (1500) in the high-power configuration even if anvil (1500) is subsequently decoupled from stapling head assembly (300). Power switch (1570) of a momentary type may be configured to transition anvil (1500) from the high-power configuration to the low-power configuration should anvil (1500) be subsequently decoupled from stapling head assembly (300).

Anvil (1500) may further comprise a shroud (1562) positioned distal to and sealingly coupled to head (1510). Shroud (1562) may include a rounded distal tip which may be useful for minimizing trauma to patient tissue in-vivo. Shroud (1562) may fluidly seal a distal portion of head (1410) so as to prevent exposure of processor (1540), battery (1550), transmitter (1555), and head sensors (1502) to outside fluids. To prevent fluid ingress, head (1510) or shroud (1560) may include a seal (1564) between head (1510) and shroud (1560). Shroud (1560) may include one or more shroud pins (1562) that fit into head pin holes (1514) of head (1510). Shroud pins (1562) may aid in alignment and positioning of shroud (1560) relative to head (1510). Head pin holes (1514) may be blind or through holes within head (1510). When head pinholes (1514) are in the through hole configuration, at least one head pin hole (1514) may also act to vent the area inside shroud (1560) where the electronics are housed. Whether vented or not, anvil (1500) may be sterilized. Shroud (1562) may be selectively removable from head (1510) and include either metal or plastic.

B. Method of Using Wireless Powered Anvil

Figure 9A:
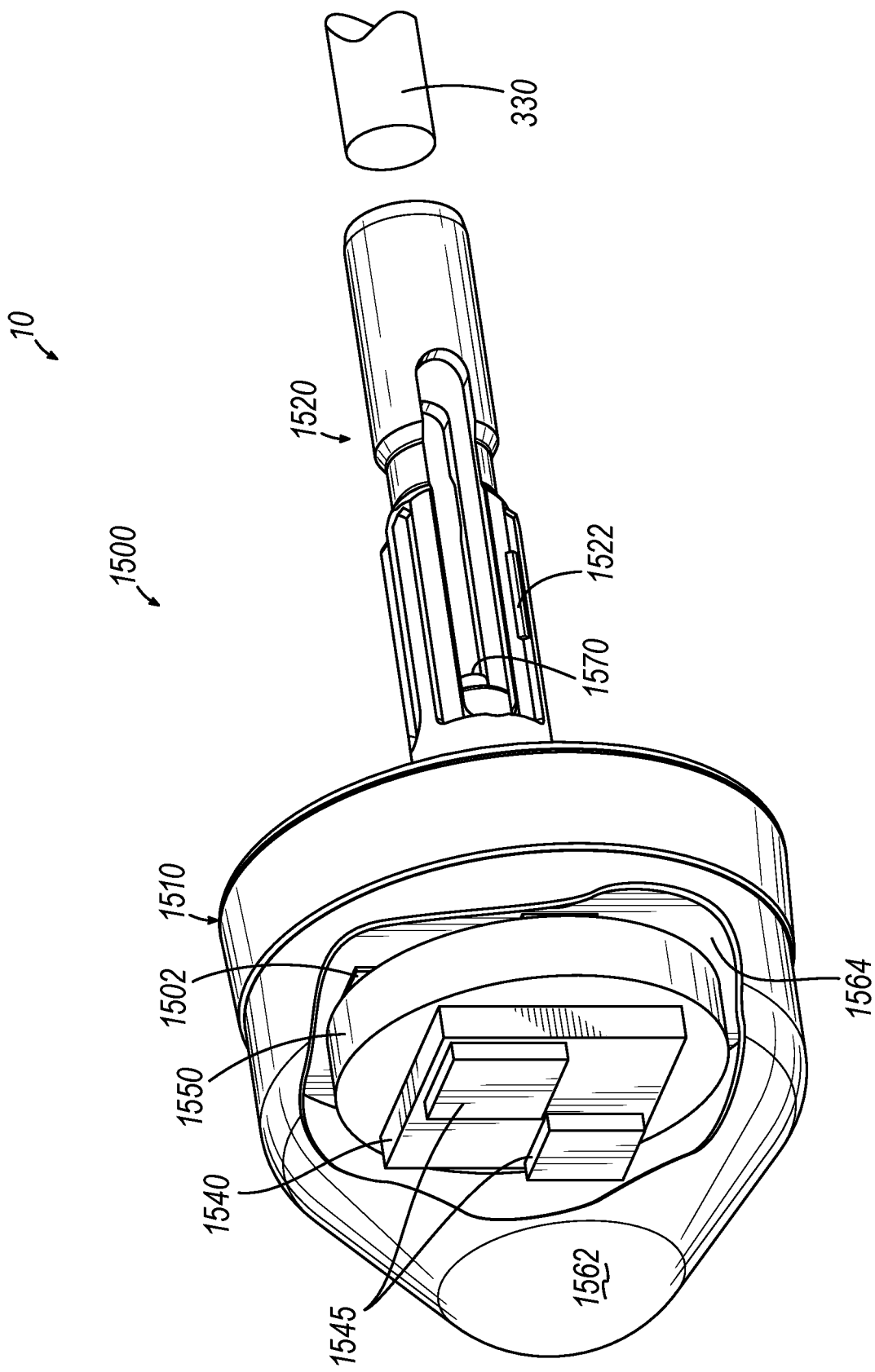
FIG. 9A depicts a perspective view of the anvil of FIG. 8 prior to being coupled with a trocar of the stapling head assembly of FIG. 4, showing the shroud partially broken away to reveal the enclosed electronic components.
Figure 9B:
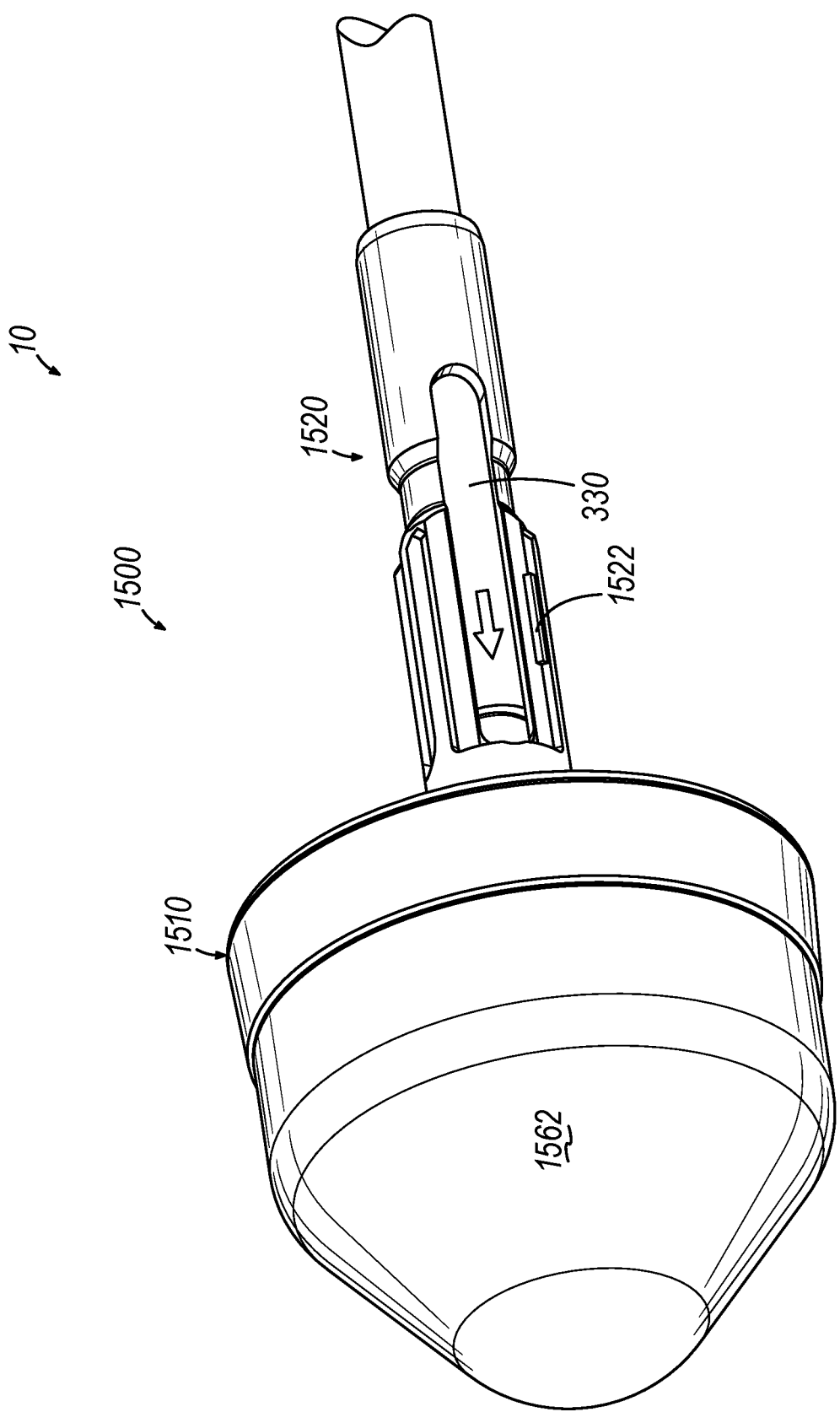
FIG. 9B depicts a perspective view of the anvil of FIG. 8 after being coupled with the trocar of the stapling head assembly of FIG. 4.

FIGS. 9A and 9B illustrate anvil (1500) being coupled with trocar (330) of stapling head assembly (300). As shown in FIG. 9A, with anvil (1500) and instrument (10) separated, power switch (1570) and the rest of anvil (1500) may be in the low-power configuration such that no wireless communication or sensor communication is performed. As trocar (330) of instrument (10) advances into shank (1520), trocar (330) may depress power switch (1570), as shown in FIG. 9B. Once pressed, power switch (1570) may communicate with remaining portions of anvil (1500) to thereby transition anvil (1500) into the high-power configuration, as described above. Once anvil (1500) has entered the high-power configuration it may remain in the high-power configuration even when anvil (1500) and instrument (10) are uncoupled, such as transitioning back to the decoupled arrangement shown in FIG. 9A. This may be helpful to deplete any remaining energy in battery (1550) and ensure a one-time use of anvil (1500). Alternatively, anvil (1500) may return to the low-power configuration to maintain energy in battery (1550) in order to perform a subsequent procedure.

III. Examples of Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical stapler comprising: a body assembly; a shaft assembly that extends distally from the body assembly; a stapling head assembly disposed at a distal end of the shaft assembly, wherein the stapling head assembly is operable to drive a plurality of staples into tissue, wherein the stapling head assembly comprises a closure shaft that is selectively movable longitudinally; and an anvil configured to form the staples, wherein the anvil is selectively coupleable with and actuatable by the closure shaft, wherein the anvil comprises: one or more sensors each configured to detect a parameter associated with at least one of closure or firing of the end effector; a processor configured to receive signals from the one or more sensors, wherein the signals are indicative of the parameter detected by the one or more sensors; a transmitter configured to transmit the signals received by the processor; and a battery configured to power the processor and the transmitter.

Example 2

The surgical stapler of Example 1, wherein the one or more sensors comprise three or more sensors.

Example 3

The surgical stapler of Example 2, wherein the three or more sensors are arranged circumferentially on the anvil to define multiple loading zones.

Example 4

The surgical stapler of Example 3, wherein each of the three or more sensors is associated with a respective one of the multiple loading zones, and wherein the parameter detected by each respective one of the three or more sensors is associated with the respective one of the multiple loading zones.

Example 5

The surgical stapler of any of the preceding Examples, wherein the one or more sensors comprise one or more strain gauges.

Example 6

The surgical stapler of Example 5, wherein the parameter detected by the one or more strain gauges comprises a strain experienced by the anvil during tissue compression.

Example 7

The surgical stapler of any of the preceding Examples, the anvil further comprising a power switch configured to transition the anvil between a low-power configuration and a high-power configuration, wherein the anvil in the low-power configuration consumes less energy from the battery than the anvil in the high-power configuration.

Example 8

The surgical stapler of Example 7, wherein the power switch is configured to contact the closure shaft of the stapling head assembly and thus transition the anvil from the low-power configuration to the high-power configuration.

Example 9

The surgical stapler of any of the preceding Examples, wherein the one or more sensors comprise one or more load cells.

Example 10

The surgical stapler of Example 9, wherein the parameter detected by the one or more load cells comprises a force applied to the tissue during tissue compression.

Example 11

The surgical stapler of any of the preceding Examples, wherein the one or more sensors are in electrical communication with the processor, and wherein the one or more sensors are configured to communicate one or more signals to the processor.

Example 12

The surgical stapler of Example 11, wherein the processor is configured to compare the one or more signals to a predetermined threshold.

Example 13

The surgical stapler of Example 12, wherein the predetermined threshold comprises a deviation from a median of the parameter detected by each of the one or more sensors.

Example 14

The surgical stapler of any of the preceding Examples, wherein the transmitter is configured to transmit the signals over Bluetooth® frequencies.

Example 15

The surgical stapler of any of the preceding Examples, wherein the anvil further comprises a shroud, a head, and a shank, wherein one or more of the one or more sensors, the processor, the transmitter, and the battery are mounted to a distal surface of the head and are enclosed by the shroud, wherein the stapling head assembly is configured to selectively couple with the shank.

Example 16

The surgical stapler of Example 15, wherein the shroud is sealingly coupled to the head and thus configured to prevent fluids from contacting one or more of the one or more sensors, the processor, the transmitter, and the battery.

Example 17

An anvil configured for use with a surgical stapler, the anvil being configured to form staples and comprising: one or more sensors each configured to detect a parameter associated with at least one of closure or firing of the surgical stapler; a processor configured to receive signals from the one or more sensors, wherein the signals are indicative of the parameter detected by the one or more sensors; a transmitter configured to transmit the signals received by the processor; a battery configured to power the processor and the transmitter; and a power switch configured to transition the anvil between a low-power configuration and a high-power configuration, wherein the anvil in the low-power configuration consumes less energy from the battery than the anvil in the high-power configuration.

Example 18

The anvil of Example 17, wherein the anvil further comprises a shroud, a head and a shank, wherein one or more of the one or more sensors, the processor, the transmitter, and the battery are mounted to a distal surface of the head and are enclosed by the shroud, wherein the stapling head assembly is configured to selectively couple with the shank.

Example 19

An anvil configured for use with a surgical stapler, comprising: a head configured to form staples; a shank configured to couple with a stapling assembly of the surgical stapler; one or more sensors mounted to the shank or the head, wherein each sensor is configured to detect a parameter associated with at least one of closure or firing of the surgical stapler; a processor configured to receive signals from the one or more sensors, wherein the signals are indicative of the parameter detected by the one or more sensors; a transmitter configured to transmit the signals received by the processor; a battery configured to power the processor and the transmitter; and a shroud configured to cover the processor, the transmitter, and the battery.

Example 20

The anvil of Example 19, the anvil further comprising a power switch configured to transition the anvil between a low-power configuration and a high-power configuration, wherein the anvil in the low-power configuration consumes less energy from the battery than the anvil in the high-power configuration.

IV. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as those made available by Auris Health, Inc. of Redwood City, CA or by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical stapler comprising:
    (a) a body assembly;
    (b) a shaft assembly that extends distally from the body assembly;
    (c) a stapling head assembly disposed at a distal end of the shaft assembly, wherein the stapling head assembly is operable to drive a plurality of staples into tissue, wherein the stapling head assembly comprises a closure shaft that is selectively movable longitudinally; and
    (d) an anvil configured to form the staples, wherein the anvil is selectively coupleable with and actuatable by the closure shaft, wherein the anvil comprises:
        (i) one or more sensors each configured to detect a parameter associated with at least one of closure or firing of the end effector;
        (ii) a processor configured to receive signals from the one or more sensors, wherein the signals are indicative of the parameter detected by the one or more sensors;
        (iii) a transmitter configured to transmit the signals received by the processor; and
        (iv) a battery configured to power the processor and the transmitter.

2. The surgical stapler of claim 1, wherein the one or more sensors comprise three or more sensors.

3. The surgical stapler of claim 2, wherein the three or more sensors are arranged circumferentially on the anvil to define multiple loading zones.

4. The surgical stapler of claim 3, wherein each of the three or more sensors is associated with a respective one of the multiple loading zones, and wherein the parameter detected by each respective one of the three or more sensors is associated with the respective one of the multiple loading zones.

5. The surgical stapler of claim 1, wherein the one or more sensors comprise one or more strain gauges.

6. The surgical stapler of claim 5, wherein the parameter detected by the one or more strain gauges comprises a strain experienced by the anvil during tissue compression.

7. The surgical stapler of claim 1, the anvil further comprising a power switch configured to transition the anvil between a low-power configuration and a high-power configuration, wherein the anvil in the low-power configuration consumes less energy from the battery than the anvil in the high-power configuration.

8. The surgical stapler of claim 7, wherein the power switch is configured to contact the closure shaft of the stapling head assembly and thus transition the anvil from the low-power configuration to the high-power configuration.

9. The surgical stapler of claim 1, wherein the one or more sensors comprise one or more load cells.

10. The surgical stapler of claim 9, wherein the parameter detected by the one or more load cells comprises a force applied to the tissue during tissue compression.

11. The surgical stapler of claim 1, wherein the one or more sensors are in electrical communication with the processor, and wherein the one or more sensors are configured to communicate one or more signals to the processor.

12. The surgical stapler of claim 11, wherein the processor is configured to compare the one or more signals to a predetermined threshold.

13. The surgical stapler of claim 12, wherein the predetermined threshold comprises a deviation from a median of the parameter detected by each of the one or more sensors.

14. The surgical stapler of claim 1, wherein the transmitter is configured to transmit the signals over Bluetooth® frequencies.

15. The surgical stapler of claim 1, wherein the anvil further comprises a shroud, a head, and a shank, wherein one or more of the one or more sensors, the processor, the transmitter, and the battery are mounted to a distal surface of the head and are enclosed by the shroud, wherein the stapling head assembly is configured to selectively couple with the shank.

16. The surgical stapler of claim 15, wherein the shroud is sealingly coupled to the head and thus configured to prevent fluids from contacting one or more of the one or more sensors, the processor, the transmitter, and the battery.

17. An anvil configured for use with a surgical stapler, the anvil being configured to form staples and comprising:
(a) one or more sensors each configured to detect a parameter associated with at least one of closure or firing of the surgical stapler;
(b) a processor configured to receive signals from the one or more sensors, wherein the signals are indicative of the parameter detected by the one or more sensors;
(c) a transmitter configured to transmit the signals received by the processor;
(d) a battery configured to power the processor and the transmitter; and
(e) a power switch configured to transition the anvil between a low-power configuration and a high-power configuration, wherein the anvil in the low-power configuration consumes less energy from the battery than the anvil in the high-power configuration.

18. The anvil of claim 17, wherein the anvil further comprises a shroud, a head and a shank, wherein one or more of the one or more sensors, the processor, the transmitter, and the battery are mounted to a distal surface of the head and are enclosed by the shroud, wherein the stapling head assembly is configured to selectively couple with the shank.

19. An anvil configured for use with a surgical stapler, comprising:
(a) a head configured to form staples;
(b) a shank configured to couple with a stapling assembly of the surgical stapler;
(c) one or more sensors mounted to the shank or the head, wherein each sensor is configured to detect a parameter associated with at least one of closure or firing of the surgical stapler;
(d) a processor configured to receive signals from the one or more sensors, wherein the signals are indicative of the parameter detected by the one or more sensors;
(e) a transmitter configured to transmit the signals received by the processor;
(f) a battery configured to power the processor and the transmitter; and
(g) a shroud configured to cover the processor, the transmitter, and the battery.

20. The anvil of claim 19, the anvil further comprising a power switch configured to transition the anvil between a low-power configuration and a high-power configuration, wherein the anvil in the low-power configuration consumes less energy from the battery than the anvil in the high-power configuration.

* * * * *